(12) United States Patent
Hitzeroth et al.

(10) Patent No.: US 12,396,789 B2
(45) Date of Patent: Aug. 26, 2025

(54) DETERMINING SHAPE OF EXPANDABLE DISTAL MEMBER OF A CATHETER

(71) Applicant: Biosense Webster (Israel) Ltd., Yokneam (IL)

(72) Inventors: Matthew Hitzeroth, Irwindale, CA (US); Meiron Atias, Irwindale, CA (US); Curt Eyster, Irwindale, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 718 days.

(21) Appl. No.: 17/484,380

(22) Filed: Sep. 24, 2021

(65) Prior Publication Data

US 2022/0117656 A1    Apr. 21, 2022

Related U.S. Application Data

(60) Provisional application No. 63/092,168, filed on Oct. 15, 2020.

(51) Int. Cl.
*A61B 18/00* (2006.01)
*A61B 18/14* (2006.01)

(52) U.S. Cl.
CPC .. *A61B 18/1492* (2013.01); *A61B 2018/0022* (2013.01); *A61B 2018/00773* (2013.01)

(58) Field of Classification Search
CPC ..... A61B 2018/00214; A61B 2018/0022–255; A61B 2018/00267; A61B 5/6853; A61B 5/6858; A61B 2018/00827; A61B 2018/00833; A61B 2018/00892; A61B 5/061; A61B 5/062; A61B 5/063
See application file for complete search history.

(56) References Cited

U.S. PATENT DOCUMENTS

| | | | |
|---|---|---|---|
| 7,410,486 B2 | 8/2008 | Fuimaono et al. |
| 7,756,576 B2 | 7/2010 | Levin |
| 7,848,787 B2 | 12/2010 | Osadchy |
| (Continued) | | | |

FOREIGN PATENT DOCUMENTS

| | | | |
|---|---|---|---|
| EP | 3808266 A1 | 4/2021 |
| JP | 2003210427 A | 7/2003 |
| (Continued) | | | |

OTHER PUBLICATIONS

Extended European Search Report and Search Opinion dated Mar. 16, 2022, from Corresponding European Application No. 21202579.5.

(Continued)

*Primary Examiner* — Linda C Dvorak
*Assistant Examiner* — Davina E. Lee

(57) ABSTRACT

A catheter and associated positioning system can include sensors and software to ascertain the extent of expansion of an expandable distal member of the catheter. Sensors on the distal member can be configured so that the system is able to determine a longitudinal dimension and a radial dimension of the distal-end assembly and determine extent of expansion of the distal member based on those metrics. At least the longitudinal dimension can be derived from advanced current localization (ACL) techniques utilizing an electrode at a distal end of the expandable distal member.

16 Claims, 5 Drawing Sheets

(56) References Cited

U.S. PATENT DOCUMENTS

| | | | |
|---|---|---|---|
| 7,869,865 B2 * | 1/2011 | Govari | A61B 5/06 600/424 |
| 8,456,182 B2 | 6/2013 | Bar-Tal et al. | |
| 9,907,610 B2 | 3/2018 | Beeckler et al. | |
| 2006/0009689 A1 * | 1/2006 | Fuimaono | A61B 5/06 600/509 |
| 2006/0173251 A1 | 8/2006 | Govari et al. | |
| 2009/0262980 A1 | 10/2009 | Markowitz et al. | |
| 2010/0079158 A1 | 4/2010 | Bar-Tal et al. | |
| 2010/0234838 A1 * | 9/2010 | Watson | A61M 25/1006 604/509 |
| 2014/0276733 A1 * | 9/2014 | VanScoy | A61B 18/1492 606/33 |
| 2018/0140807 A1 | 5/2018 | Herrera et al. | |
| 2018/0161093 A1 | 6/2018 | Basu et al. | |
| 2019/0059818 A1 | 2/2019 | Herrera et al. | |
| 2019/0117298 A1 * | 4/2019 | Beeckler | A61B 18/1492 |
| 2019/0201669 A1 | 7/2019 | Govari et al. | |
| 2019/0217065 A1 * | 7/2019 | Govari | A61M 25/1025 |
| 2019/0298441 A1 | 10/2019 | Clark et al. | |
| 2019/0350489 A1 | 11/2019 | Ludwin et al. | |
| 2020/0147295 A1 | 5/2020 | Van Niekerk et al. | |
| 2020/0155224 A1 | 5/2020 | Bar-Tal | |
| 2020/0155226 A1 | 5/2020 | Valls et al. | |
| 2020/0206461 A1 | 7/2020 | Govari et al. | |
| 2021/0113822 A1 | 4/2021 | Beeckler et al. | |

FOREIGN PATENT DOCUMENTS

| | | | |
|---|---|---|---|
| JP | 2018118042 A | 8/2018 | |
| JP | 2019202139 A | 11/2019 | |
| JP | 2020108769 A | 7/2020 | |
| JP | 2022509795 A | 1/2022 | |
| WO | WO-2018011158 A1 * | 1/2018 | A61B 5/06 |
| WO | 2020104886 A1 | 5/2020 | |

OTHER PUBLICATIONS

Notice of Reasons for Refusal with English translation dated Jun. 3, 2025, from corresponding Japanese Application No. 2021-168762.
Search Report with English translation dated Apr. 21, 2025, from corresponding Japanese Application No. 2021168762.

* cited by examiner

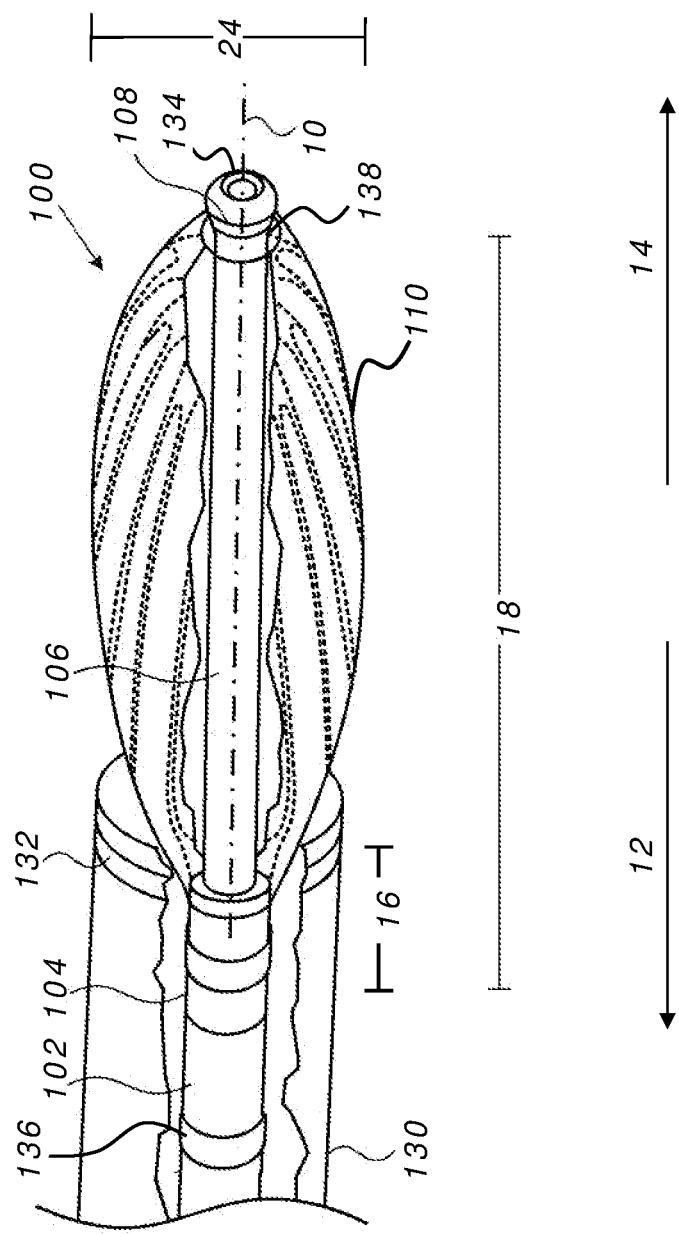

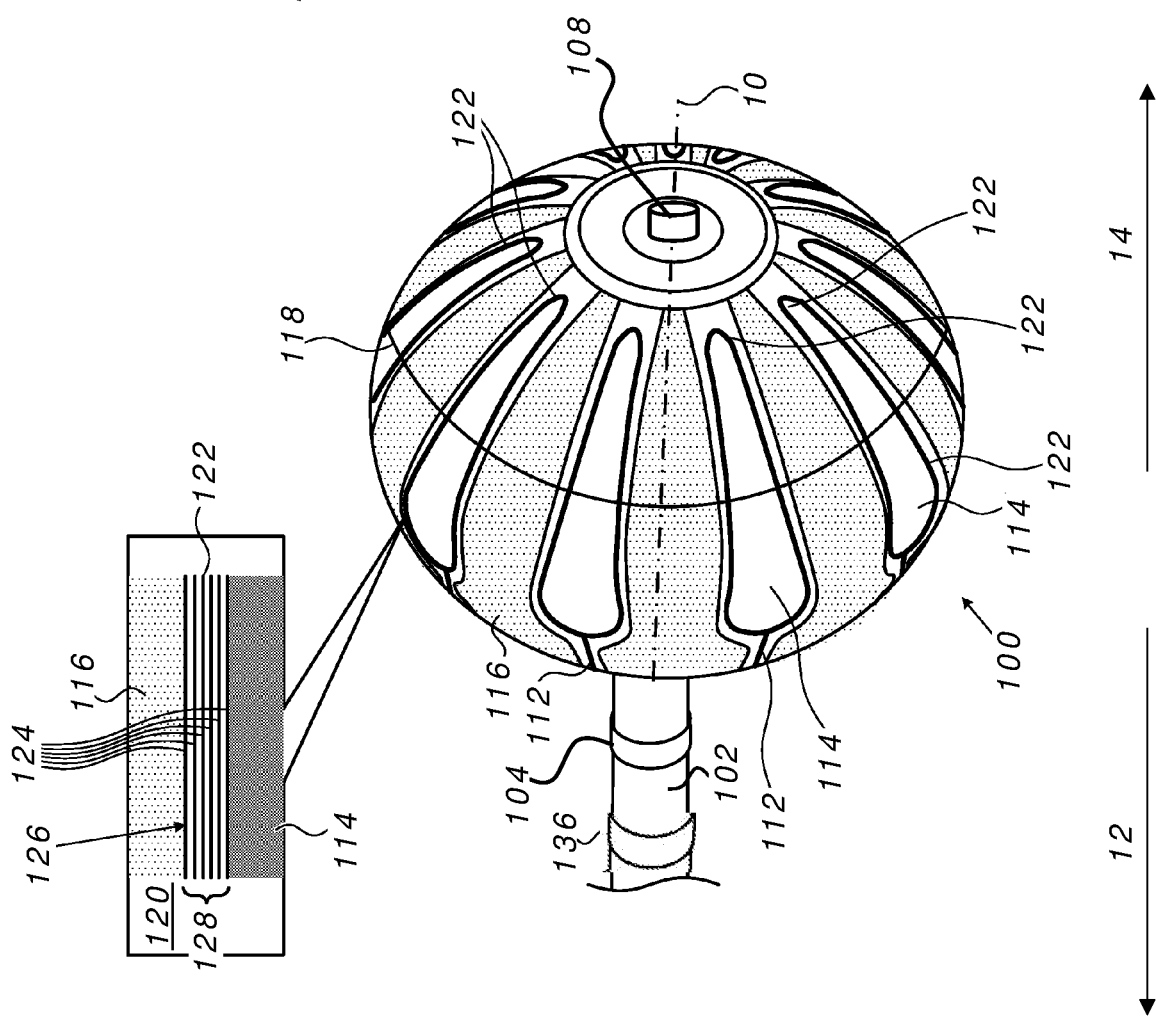

DETERMINING SHAPE OF EXPANDABLE DISTAL MEMBER OF A CATHETER

CROSS REFERENCE TO RELATED APPLICATION

This application claims the benefit of priority to prior filed U.S. Provisional Patent Application No. 63/092,168 filed on Oct. 15, 2020 which is hereby incorporated by reference as set forth in full herein.

FIELD

The present invention relates generally to medical devices and uses thereof and specifically to catheters having expandable features such as a balloon, spines, or other structure, related positioning systems, and methods of treatment utilizing such catheters and positioning systems.

BACKGROUND

Some intravascular treatments utilize catheters having an expandable distal member near a distal end of the catheter. For instance, some catheters include a balloon or spines carrying electrodes that can be used to sense and/or ablate within vasculature and/or a heart of a patient. Some of these catheters can be used in treatments involving catheter ablation of cardiac arrhythmias. There are a variety of such catheter designs usable for various purposes where, generally, the expandable distal member is collapsible to traverse vasculature and expandable within a blood vessel and/or heart. Presently, visualization of the expandable distal member on a positioning system display and physician training to property interpolate the shape, orientation, and position of the expandable distal member as presented on the display is relied on heavily during such treatments.

SUMMARY

An example catheter can include a shaft, an expandable member, and a distal sensor. The catheter can further include a proximal sensor, a navigational sensor, a telescoping member, a body sensor, and/or a trifilar wire.

The shaft can extend along a longitudinal axis of the catheter and can be manipulated to position the expandable member within a patient.

The expandable member can be positioned at a distal end of the shaft. The expandable member can be movable from an expanded configuration to a collapsed configuration. The expandable member can have a longitudinal dimension parallel to the longitudinal axis that is increased when the expandable member moves from the expanded configuration to the collapsed configuration. The expandable member can include a balloon and/or spines.

The distal sensor can be affixed to the expandable member. The distal sensor can provide electrical current to an advanced current localization tracker system and can be positioned to indicate the longitudinal dimension of the expandable member.

The proximal sensor can be affixed to the catheter in a proximal direction in relation to the distal sensor so that the distal sensor moves distally away from the proximal sensor when the expandable member moves from the expanded configuration to the collapsed configuration. The distal sensor can be positioned in relation to the proximal sensor to indicate the longitudinal dimension of the expandable member when a position of the distal sensor is compared to a position of the proximal sensor. The proximal sensor can be affixed to the shaft. The proximal sensor can provide electrical current to the advanced current localization tracker system.

The navigational sensor can be affixed approximate the proximal sensor at a static position on the catheter in relation to the proximal sensor.

The telescoping member can be engaged to the shaft and the expandable member. The telescoping member can be configured to slide along the longitudinal axis in relation to the shaft. The distal sensor can be affixed at a distal end of the telescoping member.

The body sensor can be affixed to the expandable member and positioned to indicate a radial dimension of the expandable member. The radial dimension, being perpendicular to the longitudinal axis, can be decreased when the expandable member moves from the expanded configuration to the collapsed configuration. The body sensor can include one or more conductive coils each configured as a respective magnetic sensor. The expandable member can include an expandable membrane. Each of the one or more conductive coils can be disposed over an external surface of the expandable membrane.

The trifilar wire can include three traces, at least one of which is electrically connected to the distal sensor. The trifilar wire can include two copper traces and one constantan trace.

An example catheter positioning system can include a processor and non-transitory computer readable medium in communication with the processor. The instructions can include various commands that can be executed by the processor to cause the processor to control operations of the system. The instructions can cause the processor to apply a first electrical current signal between one or more electroconductive body surface patches and a probe electrode, the electroconductive body surface patches being configured for electrical conductivity through skin of a patient, and the probe electrode being affixed to a distal expandable member of a catheter configured for insertion into the patient's body. The instructions can cause the processor to measure a first electrical voltage signal between at least one of the one or more electroconductive body surface patches and probe electrode, the first electrical voltage signal resulting from the applied first electrical current signal. The instructions can cause the processor to determine, based at least in part on the first electrical voltage signal, a length of the distal expandable member.

The instructions can cause the processor to determine a position of a proximal electrode affixed to the catheter and positioned in a proximal direction in relation the probe electrode, and determine, based at least in part on the position of the proximal electrode, the length of the distal expandable member.

The instructions can cause the processor to apply a second electrical current signal between at least one of the one or more electroconductive body surface patches and the proximal electrode and measure a second electrical voltage signal between at least one of the one or more electroconductive body surface patches and the proximal electrode, the second electrical voltage signal resulting from the applied second electrical current signal. The instructions can cause the processor to determine, based at least in part on the second electrical voltage signal, the length of the distal expandable member.

The instructions can cause the processor to compare the length to a longitudinal threshold value and provide an output indicating a change in shape of the distal expandable member when the length crosses the longitudinal threshold value. The instructions can cause the processor to compare the length to a minimum re-sheathing length, and when the length increases to exceed the minimum re-sheathing length, trigger low flow to the distal expandable member and prevent high flow being activated to inflate the distal expandable member. When the length decreases to below the longitudinal threshold value, the instructions can cause the processor to allow high flow to inflate the distal expandable member.

The instructions can cause the processor to apply a magnetic field through the patient's body, measure inductive electrical signals from a navigation sensor affixed to the catheter, and determine, based at least on the inductive electrical signals and the first electrical voltage signal, the position of the probe electrode.

The instructions can cause the processor to determine a radius of expansion of the distal expandable member. The instructions can cause the processor to compare the radius of expansion to a radial threshold value and provide an output indicating a change in shape of the distal expandable member when the radius of expansion crosses the radial threshold value. The radial threshold value can be based at least in part on a re-sheathing force calculation.

The instructions can cause the processor to receive one or more sensor signals from sensors affixed to the distal expandable member and spaced radially about the distal expandable member. The instructions can cause the processor to determine the radius of expansion based at least in part of the one or more sensor signals.

The instructions can cause the processor to compare the length to the longitudinal threshold value, compare the radius of expansion to the radial threshold value, and provide an output indicating the catheter is sufficiently collapsed to be sheathed when both the length is greater than the longitudinal threshold value and the radius of expansion is less than the radial threshold value. The longitudinal threshold value can measure about 41 millimeters (mm).

An example method can include one or more of the following steps presented in no particular order. A first electrical current signal can be applied between one or more electroconductive body surface patches and a probe electrode, the electroconductive body surface patches being configured for electrical conductivity through skin of a patient, and the probe electrode being affixed to a distal expandable member of a catheter configured for insertion into the patient's body. A first electrical voltage signal can be measured between at least one of the one or more electroconductive body surface patches and probe electrode, the first electrical voltage signal resulting from the applied first electrical current signal. A length of the distal expandable member can be determined based at least in part on the first electrical voltage signal.

The method can further include determining a position of a proximal electrode affixed to the catheter and positioned in a proximal direction in relation the probe electrode and determining, based at least in part on the position of the proximal electrode, the length of the distal expandable member.

The method can further include applying a second electrical current signal between at least one of the one or more electroconductive body surface patches and the proximal electrode; measuring a second electrical voltage signal between at least one of the one or more electroconductive body surface patches and the proximal electrode, the second electrical voltage signal resulting from the applied second electrical current signal and determining, based at least in part on the second electrical voltage signal, the length of the distal expandable member.

The method can further include comparing the length to a longitudinal threshold value and providing an output indicating a change in shape of the distal expandable member when the length crosses the longitudinal threshold value.

The method can further include applying a magnetic field through the patient's body, measuring inductive electrical signals from a navigation sensor affixed to the catheter, and determining, based at least on the inductive electrical signals and the first electrical voltage signal, a position of the probe electrode.

The method can further include determining a radius of expansion of the distal expandable member. The method can further include comparing the radius of expansion to a radial threshold value; and providing an output indicating a change in shape of the distal expandable member when the radius of expansion crosses the radial threshold value. The method can further include receiving one or more sensor signals from sensors affixed to the distal expandable member and spaced radially about the distal expandable member and determining, based at least in part of the one or more sensor signals, the radius of expansion.

The method can further include comparing the length to the longitudinal threshold value, comparing the radius of expansion to the radial threshold value, and providing an output indicating the catheter is sufficiently collapsed to be sheathed when both the length is greater than the longitudinal threshold value and the radius of expansion is less than the radial threshold value. The longitudinal threshold value can measure about 41 mm. The method can further include basing the radial threshold value at least in part on a re-sheathing force calculation.

BRIEF DESCRIPTION OF THE DRAWINGS

FIG. 1A is an illustration of a distal portion of an example catheter and sheath in a cut-away view and partially collapsed according to aspects of the present invention.

FIG. 1B is an illustration of the distal portion of the example catheter expanded with illustrated surface details according to aspects of the present invention.

DETAILED DESCRIPTION

Figure 2:
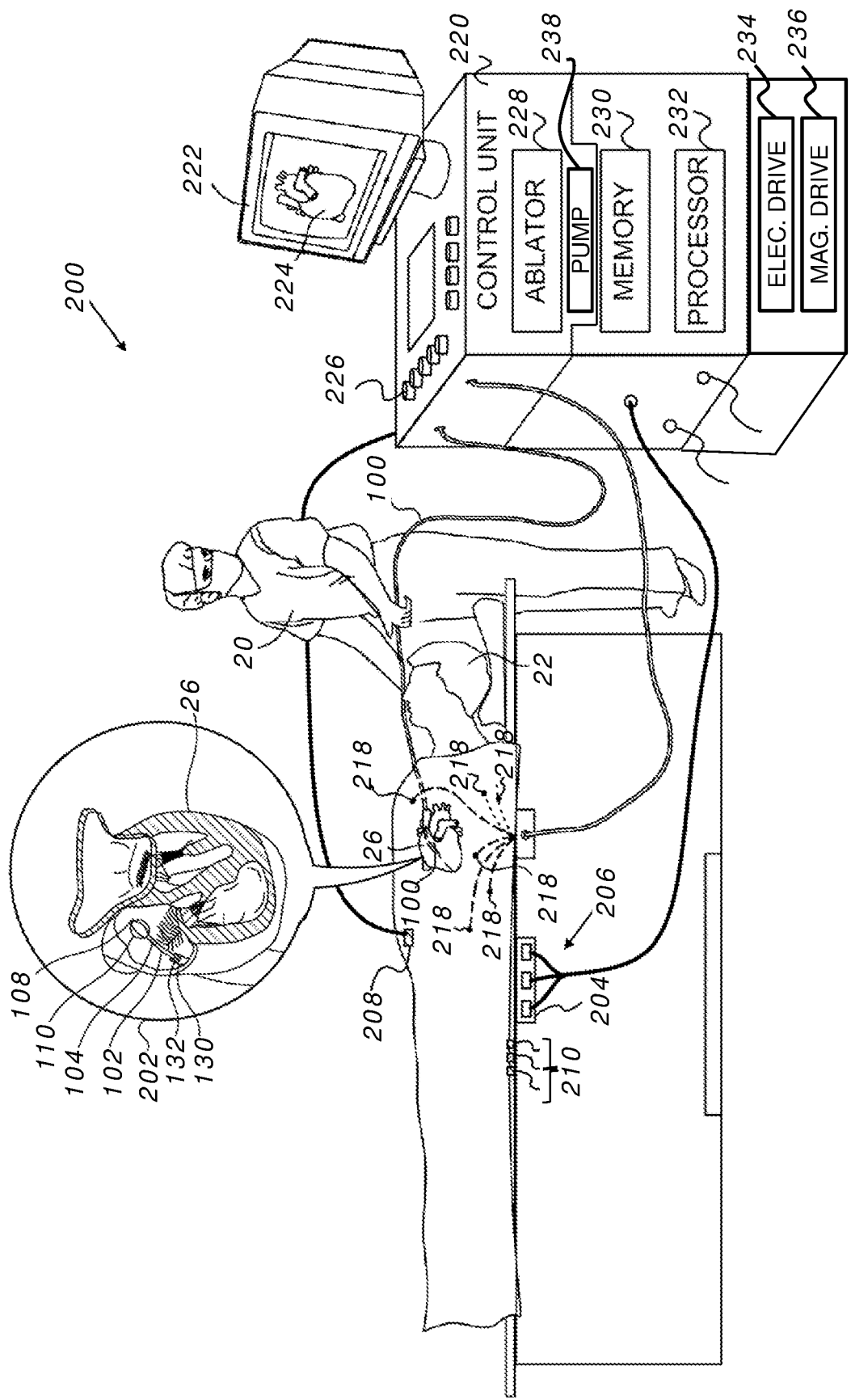
FIG. 2 is an illustration of a positioning system according to aspects of the present invention.

The following description of certain examples of the invention should not be used to limit the scope of the present invention. The drawings, which are not necessarily to scale, depict selected embodiments and are not intended to limit the scope of the invention. The detailed description illustrates by way of example, not by way of limitation, the principles of the invention. Other examples, features, aspects, embodiments, and advantages of the invention will become apparent to those skilled in the pertinent art from the following description, which includes by way of illustration, one of the best modes contemplated for carrying out the invention. As will be realized, the invention is capable of other different or equivalent aspects, all without departing from the invention. Accordingly, the drawings and descriptions should be regarded as illustrative in nature and not restrictive.

Teachings, expressions, versions, examples, etc. described herein may be combined with other teachings, expressions, versions, examples, etc. that are described herein, including those examples provided in the references attached in the Appendix to priority application U.S. 63/092, 168. The following-described teachings, expressions, versions, examples, etc. should therefore not be viewed in isolation relative to each other. Various suitable ways in which the teachings herein may be combined are apparent to those skilled in the pertinent art in view of the teachings herein. Such modifications and variations are intended to be included within the scope of the claims.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g., "about 90%" may refer to the range of values from 71% to 99%.

As used herein, the terms "patient," "host," "user," and "subject" refer to any human or animal subject and are not intended to limit the systems or methods to human use, although use of the subject invention in a human patient represents a preferred embodiment.

As used herein, the term "non-transitory computer-readable media" includes, but is not limited to, random access memory (RAM), read-only memory (ROM), electronically erasable programmable ROM (EEPROM), flash memory or other memory technology, compact disc ROM (CD-ROM), digital versatile disks (DVD) or other optical storage, magnetic cassettes, magnetic tape, magnetic disk storage or other magnetic storage devices, or any other tangible, physical medium which can be used to store computer readable information.

As used herein, the term "wire" can include elongated solid core and hollow core structures. When used to refer to an electrical conductor, the term wire "wire" can include insulated, non-insulated, individual, bundled, and integrated circuit conductors.

An expandable distal member of a catheter for insertion into a vessel or cavity of a patient such as a balloon catheter or basket catheter can be used in various clinical applications such as electro-anatomical mapping and/or ablation of vasculature or cavity walls, for example, in or around the heart. Generally, expandable distal members are collapsed when delivered through a body lumen (e.g., vasculature) to a treatment site, expanded upon arrival at the treatment site, and collapsed again for extraction or repositioning. A distal member that is insufficiently expanded may not be effective at providing treatment and movement of a distal member that is insufficiently collapsed may result in patient injury or damage to the distal member.

It can be advantageous map the position and/or shape of the catheter's expandable distal-end assembly. U.S. Pat. Nos. 7,756,576, 7,848,787, 7,869,865, and 8,456,182, each incorporated by reference herein and attached in the Appendix to priority application U.S. 63/092,168, describe mapping tools that utilize multiple tracking techniques including advanced current localization (ACL), electromagnetic (EM) systems, fluoroscopy systems, magnetic resonance imaging (MRI) systems, and ultrasound systems. U.S. Patent Publication 2020/0206461, incorporated by reference herein and attached in the Appendix to priority application U.S. 63/092, 168, describes a system for determining elongation of a distal end of a catheter. U.S. Patent Publication 2020/ 0155224, incorporated by reference herein and attached in the Appendix to priority application U.S. 63/092,168, describes configuring a perimeter of a balloon electrode as a location sensor.

In the case of a balloon catheter, the balloon is inflated and deflated by pumping a fluid (e.g., saline solution) through an inflation tube and/or lumen of the catheter. Some balloon catheters include mechanisms to facilitate the expansion and collapse of the balloon; see for example, U.S. Patent Application Publication 2018/0140807, U.S. Patent Application Publication 2018/0161093, U.S. Patent Application Publication 2019/0059818, U.S. Patent Application Publication 2019/0201669, U.S. Patent Application Publication 2019/ 0217065, U.S. Patent Application Publication 2020/ 0147295, and U.S. Pat. No. 9,907,610, each incorporated by reference herein and attached in the Appendix to priority application U.S. 63/092,168. Additional example irrigation balloons including electrodes for sensing and/or ablation are described in U.S. Patent Application Publication 2020/ 0155226, U.S. Patent Application Publication 2019/ 0298441, and U.S. Pat. No. 7,410,486, each incorporated by reference herein and attached in the Appendix to priority application U.S. 63/092,168.

In the case of an end effector or other spined structure, spines can self-expand upon exiting a sheath or delivery catheter and collapsed upon re-sheathing. Additionally, or alternatively, spined structures can be expanded mechanically via manipulation of pull wires or pull tubes (referred to herein generally as "pull wires"). See U.S. Patent Publication 2020/0155224 incorporated by reference herein and attached in the Appendix to priority application U.S. 63/092, 168.

Example catheters and associated control systems presented herein can include sensors and software to ascertain the extent of expansion of the distal member, where a potential benefit of such example catheters and systems may be to reduce likelihood of undesirable treatment outcomes resulting from an insufficiently expanded and/or insufficiently collapsed distal member. In some examples, sensors on the distal member can be configured so that the system is able to determine a longitudinal dimension and a radial dimension of the distal member and determine extent of expansion of the distal member based on those metrics. In some examples, one or both of those metrics can be derived from ACL techniques. Preferably, the catheter includes a distal electrode functioning as an ACL sensor that provide signals which can be used to derive the length of the distal member. The figures described herein include a few illustrations of how such catheters and control systems can be configured. The Appendix attached to priority application U.S. 63/092,168 includes description of related technology that can be combined according to the teachings herein to modify or replace the illustrated examples herein to measure and/or utilize the longitudinal dimension and/or radial dimension metric.

FIGS. 1A and 1B illustrate an example balloon catheter 100. The catheter 100 includes an expandable distal member 110 coupled to a distal end of a shaft 102. The shaft 102 defines a longitudinal axis 10 of the catheter 100. A proximal direction 12 and distal direction 14 are illustrated. The catheter 100 is illustrated partially collapsed in preparation for re-sheathing in FIG. 1A and in an expanded configuration in FIG. 1B. FIG. 1A is a cut-away view showing electrodes 104, 108 that can be used to determine a longitudinal dimension 18 of an expandable distal member 110 of the catheter 100. FIG. 1B is an exterior view of the expandable distal member 110 showing inductive coils 122 which can be used to determine a position and/or radial dimension 24 of the distal member 110. When the longitudinal dimension 18 and/or radial dimension 24 are within a certain range, the expandable distal member 110 can be re-sheathed with an acceptably low risk of injury to the patient and/or damage to the catheter 100. The longitudinal dimension 18 and/or radial dimension 24 can also be used to provide user feedback as to the shape and/or position of the distal expandable member 110 for purposes other than re-sheathing. The longitudinal dimension 18 and/or radial dimension 24 can also be used to provide control feedback to a control system (see FIG. 2).

The catheter 100 can include both electric and magnetic position tracking sub-systems. The electric position tracking sub-system is equivalently referred to herein as an ACL system, and the magnetic position tracking sub-system is equivalently referred to herein as an EM system. Preferably, the electric position tracking sub-system includes the distal electrode 108 and the proximal electrode 104. The magnetic position tracking sub-system preferably includes a navigation sensor 136 affixed to the shaft 102 of the catheter 100 in close proximity to the proximal sensor 104. When the electric position tracking sub-system includes the proximal electrode 104 and the magnetic tracking system includes the navigation sensor 136 as illustrated, the proximal electrode 104 and navigation sensor 136 are affixed at a known distance from each other and therefore provide a common point of reference between the two sub-systems which can be used to increase accuracy of position, shape, and/or orientation calculations based on the two sub-systems. The magnetic position tracking sub-system can include the inductive coils 122 on a balloon membrane 116. The electric tracking sub-system can include ablation electrodes 114 on the balloon membrane 116.

The proximal electrode 104, distal electrode 108, and inductive coils 122 can each respectively be reconfigured to function with either the electric or magnetic position tracking sub-systems as understood by those skilled in the pertinent art according to the teachings herein. The catheter 100 can include additional sensors and electrodes not illustrated that can be used to determine position, orientation, and/or shape of the expandable distal member 110 as understood by those skilled in the pertinent art according to the teachings herein. The catheter 100 can further be adapted according to hybrid tracking system approaches such as described in U.S. Pat. Nos. 7,756,576, 7,848,787, 7,869,865, and 8,456,182, each incorporated by reference herein and attached in the Appendix to priority application U.S. 63/092, 168.

While the distal electrode 108 can be modified to function as an inductive sensor, configuring the distal electrode 108 to instead function in the electric position tracking sub-system can require less intricate wiring and electrode geometry, particularly when the proximal electrode 104 is configured within the electric tracking sub-system. Further, catheters currently including a distal radiopaque marker at the position of the distal electrode 108 as illustrated can be modified by providing a conductor to the distal marker without requiring significant change in geometry or composition of the distal marker.

The proximal electrode 104 and distal electrode 108 are respectively connected to conductors (e.g., wires or conductive traces) extending through a shaft 102 of the catheter 100. In some examples, the conductor to the distal electrode 108 can be an independent wire. The wire can run alongside bundled wires within the shaft 102, along an ablation electrode 114, and to the distal electrode 108. Alternatively, a trifilar wire can run to an ablation electrode 114 and the distal electrode 108 where one of the conductors of the trifilar wire is a copper conductor terminating at the distal electrode 108. The conductors can be connected to a control unit 220 in a positioning system 200 as illustrated in FIG. 2. The system 200 can utilize ACL to determine the longitudinal dimension 18 by measuring distance between the proximal electrode 104 and the distal electrode 108. Functionality of the system 200 is described in greater detail in relation to FIG. 2.

Referring to FIG. 1A, the catheter 100 can include a telescoping shaft 106 that provides structural support to the balloon membrane 116 and that can be manipulated to extend or retract the balloon. The distal electrode 108 can be affixed in relation to the distal telescoping shaft 106 and at a distal end of the telescoping shaft 106. The telescoping shaft 106 can slide in and out of the catheter shaft 102 to cause the longitudinal dimension 18 of the expandable distal member 110 to foreshorten and elongate. Additionally, or alternatively, the expandable distal member 110 can include alternative structural components to facilitate controlled elongation and foreshortening of the longitudinal dimension 18 of the expandable distal member 110 such as described in U.S. Patent Application Publication 2018/0140807, U.S. Patent Application Publication 2018/0161093, U.S. Patent Application Publication 2019/0059818, U.S. Patent Application Publication 2019/0201669, U.S. Patent Application Publication 2019/0217065, U.S. Patent Application Publication 2020/0147295, and U.S. Pat. No. 9,907,610, each incorporated by reference herein and attached in the Appendix to priority application U.S. 63/092,168. For a catheter lacking a telescoping shaft 106, the distal electrode 108 can be affixed at a distal end of the balloon so that the distal electrode 108 moves longitudinally in relation to the catheter shaft 102 when the balloon is expanded and collapsed.

The catheter 100 can be retracted into a sheath 130. As illustrated, the sheath 130 can include a sheath position sensor 132 disposed on a distal end of the sheath 130. The sheath position sensor 132 can be connected by conductors to the control unit 220 of the system 200 illustrated in FIG. 2. The sheath position sensor 132 can be used to determine a position of the expandable distal member 110 in relation to a distal end of the sheath 130. For instance, the system 200 can be configured to determine a distance 16 between the proximal electrode 104 on the shaft 102 of the catheter 100 and the sheath position sensor 132. The catheter 100 and the system 200 can be configured to detect an event in which the expandable distal member 110 is being withdrawn into the sheath while still at least partially expanded as described in U.S. patent application Ser. No. 16/657,463, filed Oct. 18, 2019 and published as U.S. Patent Publication 2021/0113822 on Apr. 22, 2021, incorporated herein by reference and attached in the Appendix to priority application U.S. 63/092,168.

Referring to FIG. 1B, ablation electrodes 114 are illustrated evenly disposed over an equator 118 of the expandable membrane 116 of the expandable distal member 110. Each coil 122 is wound around the perimeter of each ablation electrode 114. The coils 122 can be disposed on a flexible printed circuit board (PCB) 126, and the flexible PCB 126 can be attached to the expandable membrane 116. Each ablation electrode 114 and a respective coil 122 can share a lead 112. As shown in inset 120, each coil 122 can be made of several turns 124 (i.e., windings). Each turn 124 of coil 122 can have a width of several tens of microns, so that the overall width 128 of the perimeter (i.e., of coil 122) is kept to no more of several hundred microns. Each ablation electrode 114 can have an area of several tens of square millimeters (mm), so that a coil 122 wound several turns around the electrode perimeter has an effective area of several hundred square mm. With present fabrication techniques, a typical width of a turn on a coil 122 is about 40 to about 50 microns, therefore six or seven turns results in an effective area of about 250 to about 350 square mm. The coils 122 can be connected to the control unit 220 (FIG. 2) to determine the radial dimension 24 of the expandable distal member 110. In some examples, the coils 122 can be used to determine a position of the expandable distal member 110, in which case the coils 122 can be used in place of, or as a supplement to, the navigation sensor 136. This functionality can be realized using a catheter and system as described in U.S. Patent Publication 2020/0155224, incorporated by reference herein and attached in the Appendix to priority application U.S. 63/092,168.

The illustrations shown in FIGS. 1A and 1B are chosen purely for the sake of conceptual clarity. Other geometries of balloons, ablation electrodes, and coils 122 are possible. The expandable distal member 110 can include additional features not illustrated, such as irrigation ports and temperature sensors, which are omitted for the sake of clarity.

FIG. 2 illustrates an example system 200 which can be used to manipulate and drive the catheter 100 in clinical applications. In an example procedure, a physician 20 can navigate the catheter 100 through vasculature to position the expandable distal member 110 within or near a heart 26 of a patient 22 (see inset 202). Additionally, or alternatively, the position sensing system 200 can be used with probes similar to the catheter 100 in other body cavities.

The system 200 can include both electric and magnetic position tracking sub-systems. As illustrated, the electric position tracking system includes body surface electrodes (ACL patches) 218 configured to interact with the electric position tracking system of the catheter 100 (e.g., electrodes 104, 108) so that impedance measurements between the ACL patches 218 and catheter electric position tracking electrodes 104, 108 can be measured. The magnetic position tracking sub-system preferably includes a location pad 204 including coils 206 configured to generate and/or receive magnetic fields in the patient 22 which interact with the magnetic position tracking sub-system of the catheter 100 (e.g., navigation sensor 136 and/or coils 122). The magnetic position tracking sub-system can further include reference patches 210 adhered to the patient's skin (as illustrated) or positioned within the patient's body as another mode of determining catheter position. The system 200 can further include an ablation patch 208 positioned on the patient 22 to provide a return path for ablation electrodes 114 of the catheter 100. The system 200 can further be adapted according to hybrid tracking system approaches such as described in U.S. Pat. Nos. 7,756,576, 7,848,787, 7,869,865, and 8,456,182, each incorporated by reference herein and attached in the Appendix to priority application U.S. 63/092, 168. Various configurations of an electric position tracking sub-system, a magnetic position tracking sub-system, and other tracking systems are described elsewhere and only briefly described herein for the sake of brevity. The system 200 can include additional components as understood by a person skilled in the pertinent art, which are omitted for the sake of clarity.

The illustrated system 200 includes a control unit 220 to drive the system 200 and provide a user interface. The illustrated control unit 220 includes a processor 232 and a memory 230. The processor 232 is in communication with components and modules of the control unit 220 including the console 222, an ablator module 228, a pump 238, an electric tracking system driver 234, and a magnetic tracking system driver 236. The processor 232 can additionally be in communication with components or modules not illustrated for the sake of brevity. The memory 230 can include instructions stored thereon that can be executed by the processor 232 to cause the processor 232, thereby the control unit 220, and thereby the system 200, to perform various functions described herein. The memory can additionally include instructions for executing additional functions not described herein for the sake of brevity, including those functions understood by a person skilled in the pertinent art. The memory 230 and processor 232 are illustrated as single functional blocks but can be distributed in practice. Likewise, the console 222, ablator module 228, pump 238, electric tracking system driver 234, and magnetic tracking system driver 236 are illustrated as integrated into a monolithic control unit 220; however, each of these components can be distinct or combined in various configurations as understood by a person skilled in the pertinent art.

The console 222 can function as a user interface to the physician 20 and can include a visual display 224 and user inputs 226 (e.g., buttons, knobs, touch screens, etc.). The ablator module 228 can provide energy to the ablation electrodes 114 of the catheter 100 and/or receive electrical signals from the electrodes 114 for diagnostic purposes. The pump 238 can provide fluidic pressure to inflate and deflate the balloon membrane 116 of the catheter 100 and can be omitted when alternative catheters lacking a balloon (see e.g., catheter 400 in FIG. 4) are used in place of the illustrated catheter 100. The electric tracking system driver 234 provides energy outputs and sensor inputs for the electric position tracking sub-system. The magnetic tracking system driver 236 provides energy outputs and sensor inputs for the magnetic position tracking sub-system.

The proximal electrode 104 and distal electrode 108 can function as isolated blood-contacting electrodes providing ACL mapping location capability with respect to an imbedded magnetic location sensor of the catheter 100, which can be the coils 122 on the balloon membrane 116 and/or the navigation sensor 136 on the shaft 102. The distal electrode 108 can be used to visualize the shape, location, and/or orientation of the expandable distal member 110 of the catheter. Particularly, the distal electrode 108 can be used to determine length 18 between the distal electrode 108 and proximal electrode 104, and thereby a longitudinal dimension of the expandable member 110. Angular location of the ablation electrodes 114 can also be used to visualize the shape, location, and/or orientation of the expandable distal member 110. Angular location of the ablation electrodes 114 can be visualized using inductive signals of the coils 122. Additionally, or alternatively, angular location of the ablation electrodes 114 can be visualized using the ablation electrodes 114 as electrodes driven by the electric tracking system driver 234 using similar techniques as applied to the distal electrode 108 and proximal electrode 104. The angular location of the ablation electrodes 114 can be used to determine the radial dimension 24 of the expandable distal member 110.

The control unit 220 can illustrate the shape and/or location of the catheter 100 on the visual display. The display 224 can also provide an indication as to whether the expandable distal member 110 is sufficiently collapsed to be re-sheathed. A color-coded visualization can be displayed on the visual display 224 (e.g., red if the expandable distal member 110 is insufficiently collapsed and green when the member 110 is sufficiently collapsed for re-sheathing). A written warning or status can be displayed on the visual display 224 (e.g., "Do Not Re-Sheath"/"Re-Sheath OK"). A system level signal based on the shape of the expandable distal member 110 can be transmitted to a pump 238 to reduce or reverse flow to the balloon membrane 116 of the catheter 100 to facilitate deflation of the expandable distal member 110. High flow from the pump 238 can be prevented when the expandable distal member 110 is extended and turn high flow off if the expandable distal member 110 is actuated to the extended position. Further, based on length of the expandable distal member 110, and relative level of fluid in the membrane 116 as determined based on the radial dimension 24, a "deflation index" can be created. The "deflation index" can be used based on characterization and validation of the to indicate that is it safe to re-sheath or reposition the expandable distal member 110. Such feedback to the physician 20 and/or control unit 220 can potentially reduce the risk of improper procedure that could damage the catheter 100 and/or injure the patient 22 by reducing reliance on the physician's interpellation of system outputs such as fluoroscopic visualization of ablation electrodes 114 and radiopaque marker in place of the distal electrode 108. In some treatments it can be difficult for the physician to accurately interpolate overall balloon length based solely on fluoroscopic visualization due to the orientation of the expandable distal member 110.

The processor 232 can drive the electric tracking system driver 234 to apply and receive the appropriate electrical signals to/from the body surface patches 218, proximal electrode 104, and distal electrode 108 so that length between the proximal electrode 104 and distal electrode 108 can be determined. For instance, a first electrical signal can be applied between the body surface patches 218 and the distal electrode, a first voltage signal can be measured resulting from the first electrical signal, a second electrical signal can be applied between the body surface patches 218 and the proximal electrode, a second voltage signal can be measured resulting from the second electrical signal, and the longitudinal dimension of the distal expandable member 110 can be determined based at least in part on the first and second voltage signals.

The processor can compare the length 18 between the proximal electrode 104 and distal electrode 108 (which corresponds to the longitudinal dimension of the distal expandable member 110) to a longitudinal threshold value. When the length or longitudinal dimension crosses the threshold value, the processor can provide an output indicating a change in shape of the distal expandable member 110. The output can be used to provide a user indication (e.g., on the display 224) and/or output an electrical signal to control the system 200.

The processor 232 can drive the magnetic tracking system driver 236 to produce a magnetic field through the patient's body and measure inductive electrical signals from a navigation sensor affixed to the catheter 100 (e.g., coils 122 and/or navigation sensor 136). Position of the distal electrode 108 can be determined based at least in part on the voltage signal received as a result of the electric tracking system driver 234 applying current between the distal electrode 108 and body surface electrodes 218 and based at least in part on the measured inductive electrical signals from the navigation sensor.

The processor 232 can determine a radius of expansion of the distal expandable member 110, where the radius of expansion is related to the radial dimension 24 illustrated in FIG. 1A. The processor can compare the radius of expansion to a radial threshold value. When the radius of expansion crosses the radial threshold value, the processor 232 can provide an output indicating a change in shape of the distal expandable member 110.

The processor 232 can receive one or more sensor signals from sensors (e.g., coils 122) affixed to the distal expandable member 110 and spaced radially about the distal expandable member 110. Based at least in part of the one or more sensor signals the processor 232 can determine the radius of expansion of the distal expandable member 110.

The processor can compare the length 18 between the proximal sensor 104 and distal sensor to the longitudinal threshold value, compare the radius of expansion to the radial threshold value, and provide an output indicating the catheter is sufficiently collapsed to be sheathed when both the length is greater than the longitudinal threshold value and the radius of expansion is less than the radial threshold value.

The threshold value can be arrived at as follows. For an expandable distal member 110 having a length 18 of about 45 mm, subtract distance from the distal end 134 of the distal electrode 108 to proximal edge 138 of distal electrode 108 (about 2 mm), subtract potential error in ACL measurement (±1 mm or 2 mm variability). This results in an estimated threshold of 41 mm minimum. For a typically sized sheath 130 and balloon membrane 116, the catheter 100 can be re-sheathed with acceptably minimal risk of damage when the length 18 measures about 38.5 mm, which is sufficiently below the 41 mm threshold that, even accounting for potential measurement error, the system 200 can be configured to provide a reliable indication that the expandable distal member 110 is sufficiently extended for re-sheathing when the measured length 18 is above the 41 mm threshold value. For the sake of discussion, in this example the length 18 at which the catheter 100 can be re-sheathed with acceptably minimal risk of damage is referred to herein as "minimal re-sheathing length". In this example, the longitudinal threshold value can measure about 41 mm. The longitudinal threshold value can be similarly calculated for other catheter geometries. Keeping with the present example, the system 200 can provide a user feedback or system feedback based on the length 18 for three possible scenarios: (1) a "balloon extended" status when the length 18 is over 41 mm; (2) a "extension transition" status when the balloon is being extended, the length 18 surpasses 38.5 mm and while the length 18 is below the 41 mm threshold; and (3) a "balloon retraced" status when the balloon is being retracted and crosses below the 41 mm threshold. The numerical values of length 18 in the example scenarios can be dependent on the specific catheter and sheath geometry.

The radial threshold value can be based at least in part on a re-sheathing force calculation and, like the longitudinal threshold value, can be specific to the geometry of the catheter 100 and sheath 130. Comparison of the radial dimension 24 to the radial threshold value can provide an alternative or supplemental means for determining deflation of the balloon membrane 116. Other techniques which can be used to determine deflation include plotting flow rate, balloon length, and wait time against peak re-sheathing force. Likewise, the radial dimension 24 can be plotted against peak re-sheathing force to determine the radial threshold value. The system 200 can further provide a user feedback or system feedback based on radial dimension 24 for two possible scenarios: (1) a "balloon pressurized" status when the radial dimension 24 is greater than the radial threshold; and (2) a "balloon depressurized" status when the radial dimension 24 is less than the radial threshold.

The catheter 100 can be considered sufficiently collapsed to be re-sheathed when both the "balloon extended" and "balloon depressurized" status are active. The "balloon extended" and "extension transition" status can trigger low flow and prevent high flow being activated on the pump 238. The "balloon retracted" status can allow high flow on the pump 238. The "balloon pressurized" status can cause a system indicator on pressure and can be used in conjunction with the deflation index. The "balloon depressurized" status can cause a system indicator on pressure.

Table 1 illustrates an example balloon deflation index logic matrix relying on the above-described "balloon extended", "extension transition", "balloon retracted", "balloon pressurized", and "balloon depressurized" statuses. In Table 1 length 18 is abbreviated "LD", radial dimension 24 is abbreviated "RD", and the radial threshold is represented by variable "Y". In Table 1, the longitudinal threshold value is set to 41 mm and the minimal re-sheathing length is set to 38.5 mm, following the above-described example. These values can vary depending on specifics of geometry of the expandable member 110 and sheath 130. Table 1 includes example system outputs corresponding to each status by column and by row. Additionally, the system can provide an indication that the distal expandable member 110 is sufficiently collapsed to be re-sheathed when both the "balloon extended" and "balloon depressurized" statuses are active as indicated by the * annotation. For all other combinations of statuses, the system can provide an indication that the distal expandable member 110 is not sufficiently collapsed to be re-sheathed as indicated by the † annotation.

TABLE 1

| Balloon Deflation Index Logic Matrix | | | | |
|---|---|---|---|---|
| | Balloon Extended | Extension Transition | Balloon Retracted | System Output |
| Balloon Pressurized | LD > 41 mm RD ≥ Y † | 41 mm ≥ LD > 38.5 mm RD ≥ Y † | 41 mm ≥ LD RD ≥ Y † | System Indicator on pressure; could be used in conjunction with inflation index |
| Balloon Depressurized | LD > 41 mm RD < Y * | 41 mm ≥ LD > 38.5 mm RD < Y † | 41 mm ≥ LD RD < Y † | System Indicator on pressure |
| System Output | Trigger low flow and prevent high flow being activated on pump | Trigger low flow and prevent high flow being activated on pump | Allow high flow on pump | *Re-Sheath OK; System Indicator  †Do not Re-Sheath; System Indicator |

Figure 3:
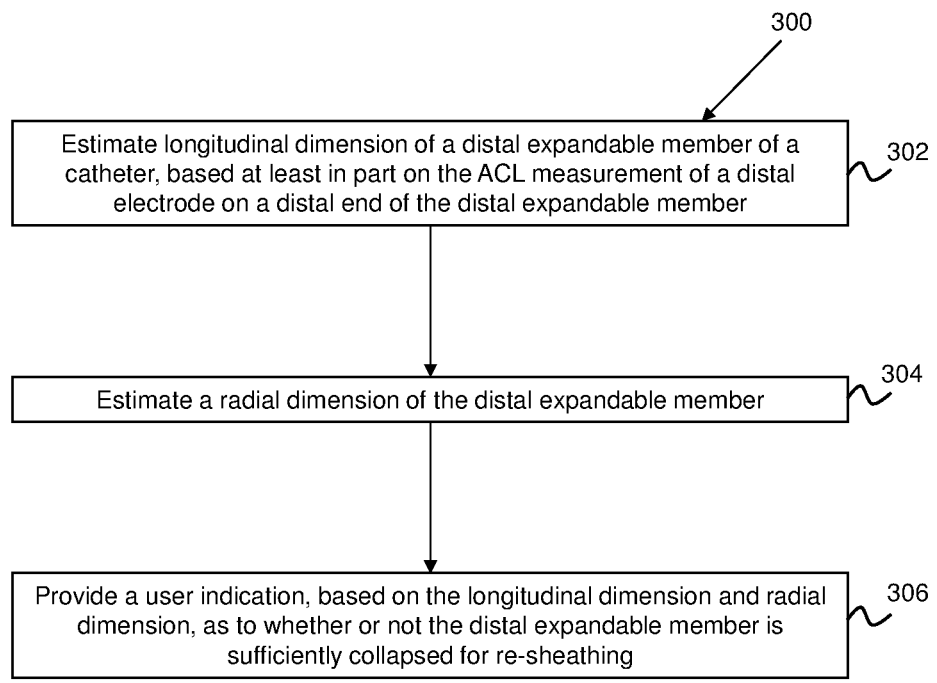
FIG. 3 is a flow diagram outlining method steps according to aspects of the present invention.
Figure 4:
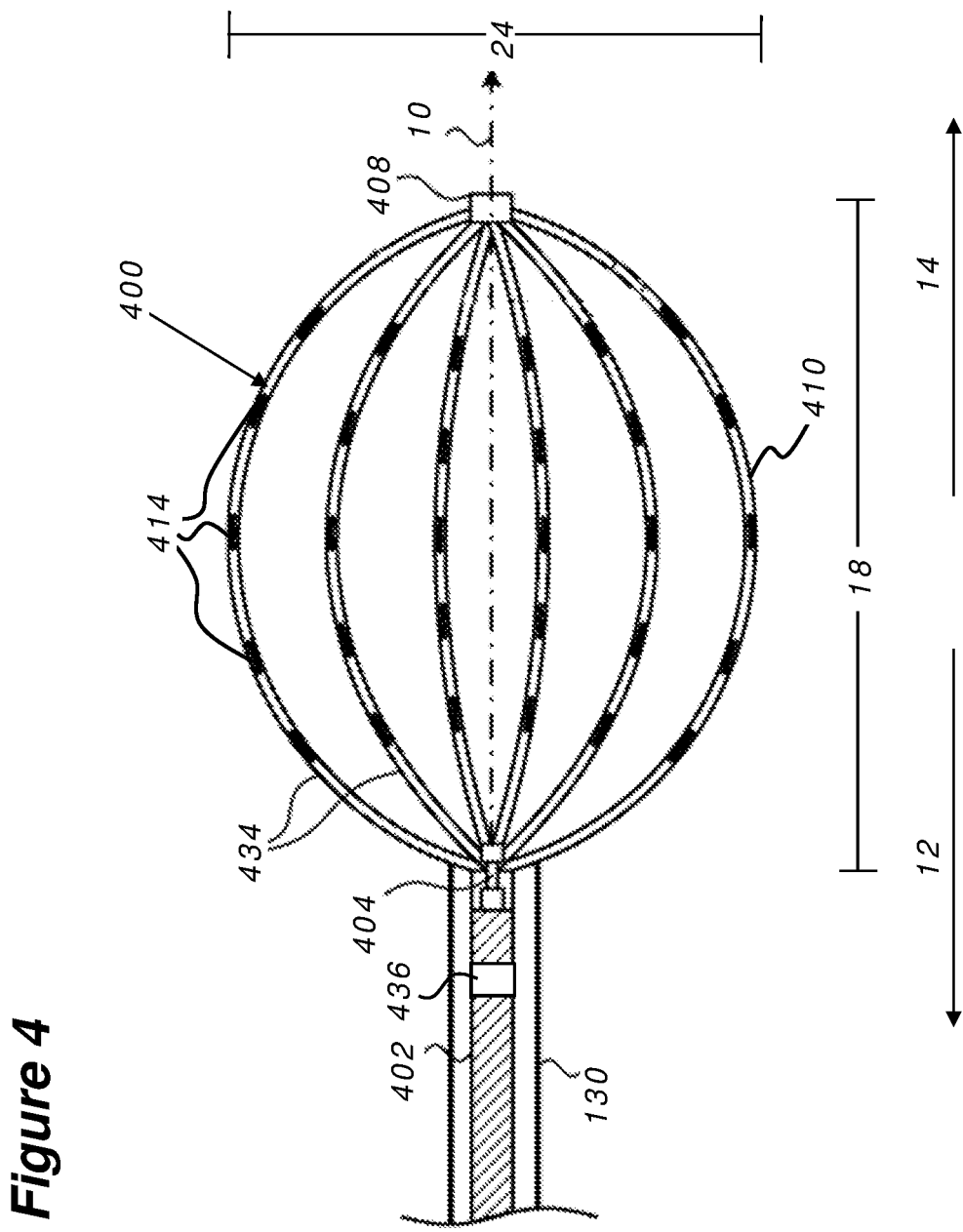
FIG. 4 is an illustration of a distal portion of another example catheter according to aspects of the present invention.

FIG. 3 illustrates a flow diagram of a method 300 that can be used during treatment to determine whether or not a distal expandable member of a catheter is sufficiently collapsed for re-sheathing with acceptable risk of damage to the distal expandable member. Method steps can also be modified to determine the shape of the distal expandable member for other purposes such as sufficient expansion to juxtapose a treatment area or sufficient collapse for movement from one treatment area to another while outside a sheath. The method can be carried out using the system 200 illustrated in FIG. 2 and the catheter 100 illustrated in FIGS. 1A and 1B, variations thereof, and alternatives thereto as understood by a person skilled in the pertinent art according to the teachings herein. For instance, the catheter 400 is illustrated in FIG. 4 can be used in place of the catheter 100 illustrated in FIGS. 1A and 1B.

At step 302, a longitudinal dimension of the distal expandable member is estimated based at least in part on an ACL measurement of a distal electrode on a distal end of the distal expandable member. The longitudinal dimension is relative to a longitudinal axis of the catheter, such as the axis 10 of catheter 100 illustrated in FIG. 1A. The distal expandable member can be configured as the distal expandable member 110 illustrated in FIGS. 1A and 1B, the distal expandable member 410 illustrated in FIG. 4, an alternative thereto, or a variation thereof as understood by a person skilled in the pertinent art. The distal electrode can be configured similar to the distal electrode 108 illustrated in FIGS. 1A and 1B, the distal electrode 408 illustrated in FIG. 4, an alternative thereto, or a variation thereof as understood by a person skilled in the pertinent art.

The ACL measurement can include applying a first electrical current signal between one or more electroconductive body surface patches and the distal electrode and measuring a first electrical voltages signal between the one or more electroconductive body surface patches and the distal electrode, the first electrical voltage signal resulting from the applied first electrical current signal. Impedance between the distal electrode and body surface patches can be calculated based on the first electrical current signal and first electrical voltage signal. The longitudinal dimension (i.e., length) of the distal expandable member can be determined based at least in part on the first electrical voltage signal (e.g., based on the calculated impedance). The electroconductive body surface patches can be configured for electrical conductivity through skin of a patient similar to the ACL patches 218 illustrated in FIG. 2 or otherwise configured as understood by a person skilled in the pertinent art.

The longitudinal dimension can also be estimated based in part on a position of a proximal electrode that is affixed to the catheter and positioned in a proximal direction in relation to the distal electrode. The proximal electrode can be configured similar to the proximal electrode 104 illustrated in FIGS. 1A and 1B, the proximal electrode 404 illustrated in FIG. 4, an alternative thereto, or a variation thereof as understood by a person skilled in the pertinent art. The position of the proximal electrode can be determined in relation to the distal electrode and/or in relation to another reference affixed to the patient or affixed in relation to the patient. A second electrical current signal can be applied between at least one of the one or more electroconductive body surface patches and the proximal electrode. A second electrical voltage signal can be measured between at least one of the one or more electroconductive body surface patches and the proximal electrode, the second electrical voltage signal resulting from the applied second electrical current signal. The longitudinal dimension can be determined based at least in part on the second electrical voltage signal (e.g., based on a calculated impedance between the proximal electrode and body surface patches).

At step 304, a radial dimension of the distal expandable member can be estimated. The radial dimension is orthogonal to the longitudinal axis of the catheter such as the radial dimension 24 illustrated in FIG. 1A. The radial dimension is therefore proportionally related to a radius of expansion of the expandable distal member. The radial dimension can be determined by various methods including those described elsewhere herein, alternatives thereto, and variations thereof as understood by a person skilled in the pertinent art. For instance, one or more sensor signals can be received from sensors affixed to the distal expandable member and spaced radially about the distal expandable member, and the radius of expansion can be determined based at least in part of the one or more sensor signals.

At step 306, a user indication can be provided as to whether or not the distal expandable member is sufficiently collapsed for re-sheathing based at least in part on the longitudinal dimension and the radial dimension estimated at steps 302 and 304. To determine whether or not the distal expandable member is sufficiently collapsed the radius of expansion can be compared to a radial threshold value and the longitudinal dimension can be compared to a longitudinal threshold value. The distal expandable member can be considered sufficiently collapsed when the radius of expansion is less than the radial threshold value and the longitudinal dimension is greater than the longitudinal threshold value. For the catheter 100 illustrated in FIGS. 1A and 1B having dimensions suitable for use in the treatment illustrated in FIG. 2, the longitudinal threshold value can measure about 41 mm. The radial threshold value can be based at least in part on a re-sheathing force calculation (i.e., amount of pull force to bring the expandable distal member into a sheath as a function of radial dimension of the expandable distal member).

Although not specifically illustrated in the flow diagram, several other useful user indications or system feedback control can be implemented based on the estimated longitudinal dimension and/or the radial dimension. For instance, an output indicating a change in shape of the distal expandable member when the radius of expansion crosses the radial threshold value can be provided. A change in shape of the distal expandable member can be indicated when the longitudinal dimension crosses the longitudinal threshold value.

The position and orientation of the distal expandable member in relation to patient anatomy can also be visualized. In some examples, magnetic navigation sensors can be used to achieve this visualization. A magnetic field can be applied through the patient's body and inductive electrical signals from a navigation sensor affixed to the catheter can be measured. In some examples, the position of the distal electrode can be determined based at least on the inductive electrical signals and the first electrical voltage signal (from ACL technique).

FIG. 4 illustrates an alternative catheter 400 that can be used in place of the catheter 100 in the system 200 illustrated in FIG. 2. The catheter 400 includes a shaft 402, navigation sensor 436, proximal electrode 404, and distal electrode 408 configured similarly to the corresponding structures 102, 136, 104, 108 of the catheter 100 illustrated in FIGS. 1A and 1B. In place of the balloon membrane 116 of the catheter 100 illustrated in FIGS. 1A and 1B, the catheter 400 illustrated in FIG. 4 includes spines 434 on a distal expandable member 410. The spines 434 carry electrodes 414 that can be driven to ablate and/or can be used to sense intracardiac electrical signals. The electrodes 414 can be supplemented or replaced by other sensors such as ultrasound transducers. The spines 434 can self-expand and can be collapsed by force from the sheath 130 against the spines 434 when the expandable distal member 410 is pulled in the proximal direction 12 into the sheath 130.

The deployment of the expandable distal member 410 is usually accomplished manually. Using techniques lacking measurement of the longitudinal dimension 18 and radial dimension 24, it difficult to know the exact measure of the expandable distal member shape, such as ellipticity, inside the cavity, as there is little (e.g., indirect) indication whether the expandable distal member 410 has fully expanded inside the cavity. When, for example, basket ellipticity is not well known, measurement results relying on a known ellipticity may produce distorted results. For example, signals from ultrasound transducers that are fitted on a plurality of expandable spines 434 of the basket 410 may be calibrated incorrectly due to a wrongly assumed basket ellipticity that, for example, causes error in assumed relative positions and orientations of the ultrasound transducers, and may cause a processor to produce a distorted anatomical map of the cavity.

To address this issue, the proximal electrode 404 and the distal electrode 408 can be used similarly to as described in relation to the proximal electrode 104 and distal electrode 108 of the catheter 100 illustrated in FIGS. 1A and 1B to determine the longitudinal dimension 18 of the catheter 400. Preferably, the distal electrode 408 is configured to function with an ACL (electric) positioning system. More preferably, both the distal electrode 408 and proximal electrode are configured to function with an electric position tracking sub-system and the navigation sensor is configured to function with a magnetic position tracking sub-system. Basket ellipticity can be estimated based on the longitudinal dimension 18. When used with the system 200, the system 200 can be configured to provide user indications and system feedback based on a longitudinal threshold value similarly to as described elsewhere herein.

The catheter 400 can optionally be outfitted with sensors to determine the radial dimension 24. For instance, the electrodes 414 can be configured to function with the electric positioning sub-system and/or inductive coils can be added to the spines 434 and configured to function with the magnetic position tracking sub-system. The radial dimension 24 can be determined similarly to as described elsewhere herein. A radial threshold value can be used to provide user and/or system feedback similarly to as described elsewhere herein.

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer-readable medium for execution by a computer or processor. Examples of computer-readable media include electronic signals (transmitted over wired or wireless connections) and computer-readable storage media. Examples of computer-readable storage media include, but are not limited to, a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

What is claimed is:

1. A catheter system comprising:
a shaft extending along a longitudinal axis of the catheter;
an expandable member comprising an expandable membrane and disposed at a distal end of the shaft, movable from an expanded configuration to a collapsed configuration, and comprising a longitudinal dimension parallel to the longitudinal axis that is increased when the expandable member moves from the expanded configuration to the collapsed configuration, the expandable membrane configured to be inflated with irrigation fluid via a pump;
a plurality of ablation electrodes disposed along the expandable membrane;
a plurality of conductive coils disposed along the expandable membrane, each respective conductive coil of the plurality of conductive coils extending around a perimeter of a respective ablation electrode of the plurality of ablation electrodes and configured as a respective to output position signals when subjected to a magnetic field;
one or more processors; and
a memory in communication with the one or more processors and storing instructions that, when executed by the one or more processors, are configured to cause the one or more processors to:
determine, based at least in part on the position signals from the plurality of conductive coils, a radius of expansion of the expandable member; and
in response to determining that the radius of expansion is greater than a minimum re-sheathing radius of expansion, output a control signal to cause the pump to output the irrigation fluid to the expandable member at a flow rate that is less than a predetermined flow rate.

2. The catheter system of claim 1, further comprising:
a distal sensor affixed to a distal portion of the expandable member and configured to provide electrical current to a current localization tracker system; and
a proximal sensor affixed to the shaft in a proximal direction in relation to the distal sensor so that the distal sensor moves distally away from the proximal sensor as the expandable member moves from the expanded configuration to the collapsed configuration,
wherein the distal sensor is positioned in relation to the proximal sensor to indicate the longitudinal dimension of the expandable member.

3. The catheter system of claim 1, further comprising:
a navigational sensor affixed proximate the proximal sensor at a static position on the catheter in relation to the proximal sensor.

4. The catheter system of claim 2, further comprising:
a telescoping member engaged to the shaft, engaged to the expandable member and configured to slide along the longitudinal axis in relation to the shaft, the distal sensor being affixed proximate a distal end of the telescoping member.

5. The catheter system of claim 1, wherein the radius of expansion is decreased when the expandable member moves from the expanded configuration to the collapsed configuration.

6. The catheter system of claim 1, the expandable member comprising a balloon.

7. The catheter system of claim 2, further comprising:
a trifilar wire comprising three traces including two copper traces and one constantan trace, one of the three traces being electrically connected to the distal sensor.

8. A catheter positioning system comprising:
a processor; and
non-transitory computer readable medium in communication with the processor with instructions thereon that, when executed by the processor, cause the processor to:
apply a first electrical current signal between one or more electroconductive body surface patches and a probe electrode, the electroconductive body surface patches being configured for electrical conductivity through skin of a patient, and the probe electrode being affixed to a distal expandable member of a catheter configured for insertion into the patient's body;
apply a second electrical current signal between the one or more electroconductive body surface patches and a proximal electrode, the proximal electrode being affixed to a shaft of the catheter;
measure a first electrical voltage signal between at least one of the one or more electroconductive body surface patches and the probe electrode, the first electrical voltage signal resulting from the applied first electrical current signal;
measure a second electrical voltage signal between at least one of the one or more electroconductive body surface patches and the proximal electrode, the second electrical voltage signal resulting from the applied second electrical current signal;
determine, based at least in part on the first electrical voltage signal and the second electrical voltage signal, a length of the distal expandable member; and
in response to determining that the length is greater than a minimum re-sheathing length:
output a control signal to cause a pump to output a flow rate to the distal expandable member that is less than a predetermined flow rate threshold, and
output, for display, an indication that the catheter is sufficiently collapsed to be sheathed.

9. The catheter positioning system of claim 8, the non-transitory computer readable medium further comprising instructions, that when executed by the processor, cause the processor to:
compare the length to a longitudinal threshold value, and
provide an output indicating a change in shape of the distal expandable member when the length is less than the longitudinal threshold value.

10. The catheter positioning system of claim 9, the non-transitory computer readable medium further comprising instructions, that when executed by the processor, cause the processor to:
when the length increases to exceed the minimum re-sheathing length, prevent a flow rate greater than the predetermined flow rate threshold from being activated to inflate the distal expandable member.

11. The catheter positioning system of claim 9, the non-transitory computer readable medium further comprising instructions, that when executed by the processor, cause the processor to:
when the length decreases to less than the longitudinal threshold value, allow a flow rate greater than the predetermined flow rate threshold to inflate the distal expandable member.

12. The catheter positioning system of claim 9, the non-transitory computer readable medium further comprising instructions, that when executed by the processor, cause the processor to:
    determine a radius of expansion of the distal expandable member.

13. The catheter positioning system of claim 12, the non-transitory computer readable medium further comprising instructions, that when executed by the processor, cause the processor to:
    compare the radius of expansion to a radial threshold value, and
    output, for display, an indication indicating a change in shape of the distal expandable member when the radius of expansion crosses the radial threshold value.

14. The catheter positioning system of claim 13, the non-transitory computer readable medium further comprising instructions, that when executed by the processor, cause the processor to:
    receive one or more sensor signals from sensors affixed to the distal expandable member and spaced radially about the distal expandable member, and
    determine, based at least in part of the one or more sensor signals, the radius of expansion.

15. The catheter positioning system of claim 13, the non-transitory computer readable medium further comprising instructions, that when executed by the processor, cause the processor to:
    in response to determining that both the length is greater than the minimum re-sheathing length and the radius of expansion is less than the radial threshold value, output, for display, an indication indicating the catheter is sufficiently collapsed to be sheathed.

16. The catheter positioning system of claim 15, the radial threshold value being based at least in part on a re-sheathing force calculation.

* * * * *